(12) United States Patent
Rawert et al.

(10) Patent No.: US 6,322,812 B1
(45) Date of Patent: Nov. 27, 2001

(54) PHARMACEUTICAL FORMS FOR THE ORAL ADMINISTRATION OF MESNA

(75) Inventors: Jurgen Rawert, Alzenau; Werner Sarlikiotis, Bielefeld, both of (DE)

(73) Assignee: ASTA Medica AG, Dresden (DE)

( * ) Notice: Subject to any disclaimer, the term of this patent is extended or adjusted under 35 U.S.C. 154(b) by 0 days.

(21) Appl. No.: 09/300,291

(22) Filed: Apr. 27, 1999

(30) Foreign Application Priority Data

Apr. 27, 1998 (DE) .............................. 198 18 804

(51) Int. Cl.[7] .............................. A61K 9/20; A61K 9/28; A61K 9/16
(52) U.S. Cl. .................. 424/464; 424/465; 424/474; 424/489; 424/490
(58) Field of Search ..................... 424/464, 465, 424/489, 474, 475, 490, 476, 479, 482

(56) References Cited

U.S. PATENT DOCUMENTS

| 5,252,341 | 10/1993 | Sauerbier et al. | 424/489 |
| 5,503,845 | 4/1996 | Goede et al. | 424/464 |

FOREIGN PATENT DOCUMENTS 0 468 245    1/1992   (EP) .

*Primary Examiner*—James M. Spear
(74) *Attorney, Agent, or Firm*—Pillsbury Winthrop LLP

(57) ABSTRACT

The invention relates to pharmaceutical forms for oral administration in the form of tablets, film-coated tablets, pellets or granules comprising at least 88% of mesna, produced by granulation with up to 15% of water, based on the amount of solid employed, and also tablets, film-coated tablets, pellets or granules comprising at least 80% of mesna, produced by direct compression or compaction, without the use of organic solvents.

6 Claims, No Drawings

PHARMACEUTICAL FORMS FOR THE ORAL ADMINISTRATION OF MESNA

This application is based on application no. 198 18 804.8 filed in Germany on Apr. 27, 1998, the content of which is incorporated hereinto by reference.

Mesna is a known antidote, which is employed for the prophylaxis of the urotoxicity of oxaphosphorines such as ifosphamide and cyclophosphamide. In addition to parenteral formulations, oral formulations are also already known.

Thus in U.S. Pat. No. 5,503,845, oral formulations in the form of tablets, pellets, capsules having an active compound content of up to >85% of mesna in combination with a preparation process of moist granulation with more than 30% of water, based on the amount of the solids employed, are described. Problems here are the long and uneconomical drying times to be expected as a result of the large amounts of water. Moreover, high amounts of water also lead to active compound instability.

Effervescent tablets with 10–80% of mesna are furthermore disclosed in U.S. Pat. No. 5,358,718. U.S. Pat. No. 5,262,169 describes tablets with 10–80% of mesna.

In both abovementioned patent specifications, the claimed composition is coupled with an alcoholic granulation process.

The use of organic liquids in granulation, however, is to be classified as problematical, since these substances are usually environmentally harmful, and moreover special arrangements are needed for employee protection.

EP 0468245 describes mesna tablets which contain 10–80% of mesna, in combination with various auxiliaries. Here too, a process for the production of these tablets by means of granulation in the presence of organic solvents is described. The same problems apply as with the abovementioned U.S. patents.

The object is thus to produce mesna tablets by means of a simple, economical production method and to do this, if possible, without the use of organic solvents.

Since mesna is administered in high doses, it is necessary for the oral mesna formulations to have an active compound content of over 80%.

Surprisingly, it was possible to achieve the object mentioned by producing pharmaceutical forms for oral administration in the form of tablets, film-coated tablets, pellets or granules comprising at least 88% of mesna, by granulation with up to 15% of water, based on the amount of solid employed, or pharmaceutical forms for oral administration in the form of tablets, film-coated tablets, pellets or granules comprising at least 80% of mesna by direct compression or compaction.

It is to be emphasized that the process for the production of pharmaceutical forms for oral administration in the form of tablets, film-coated tablets, pellets or granules by granulation, direct compression or compaction manages without the use of organic solvents.

The invention is illustrated in greater detail by means of the following working examples without, however, being restricted thereby.

EXAMPLE 1
Tablets with 100% of Mesna 500 g of mesna are sieved and moistened with 97 g of water (=19.4% based on the solid). The mixture is then granulated, and dried at 40° C. on racks. The granules are compressed to give tablets.

Weight: 500 mg

Breaking strength: 70–80 N

Disintegration: <1.5 min.

EXAMPLE 2
Tablets with 88% of Mesna
Pure Aqueous Granulation with 5.6% of Water 2.7 g of corn starch are dissolved in 3.3 g of water and swollen in 13.7 g of water.

300 g of mesna are sieved and kneaded together with swollen corn starch.

The moist mass is granulated and dried at 40° C. on racks. The dried granules are mixed with 27.0 g of microcrystalline cellulose and 6.0 g of corn starch. 2.7 g of magnesium stearate are then added and mixing is carried out again.

Weight: 225.6 mg

Breaking strength: 100 N

Disintegration: <4 min.

EXAMPLE 3
Tablets with 81.6% of Mesna
Compaction 200 g of mesna are sieved together with 30.0 g of lactose and 10.0 g of highly disperse silica and mixed. 5.0 g of magnesium stearate are then added and mixing is carried out again. The mass prepared in this way is compressed to give pressed tablets. The pressed tablets are comminuted and sieved. The material resulting in this way is mixed and processed to give tablets.

Weight: 245 mg

Breaking strength: 50 N

Disintegration: <3 min.

What is claimed is:

1. Pharmaceutical forms for oral administration in the form of tablets, film-coated tablets, pellets or granules comprising at least 88% of mesna, produced by granulation with up to 15% of water, based on the amount of solid employed, whereby a tablet of 225.6 mg weight has a breaking strength of 100 N and a disintegration time of <4 minutes.

2. Pharmaceutical forms for oral administration in the form of tablets, film-coated tablets, pellets or granules comprising at least 80% of mesna, produced by direct compression or compaction, whereby a tablet of 245 mg has a breaking strength of 50 N and a disintegration time of <3 minutes.

3. Process for the production of pharmaceutical forms for oral administration in the form of tablets, film-coated tablets, pellets or granules comprising at least 88% of mesna, by granulating the mesna with up to 15% water, based on the amount of solid employed, without the use of organic solvents.

4. Process for the production of pharmaceutical forms for oral administration in the form of tablets, film-coated tablets, pellets or granules comprising at least 80% of mesna, by directly compressing or compacting the mesna without addition of organic solvents or water.

5. Pharmaceutical forms for oral administration in the form of tablets, film-coated tablets, pellets or granules comprising 100% of mesna, produced by granulating the mesna with about 19% water, based on the amount of solid employed, whereby a tablet of 500 mg weight has a breaking strength of 70–80 N and a disintegration time of <1.5 minutes.

6. Process for the production of pharmaceutical forms for the oral administration in the form of tablets, film-coated tablets, pellets or granules comprising 100% of mesna, by granulating the mesna with up to 19% water, based on the amount of solid employed, without the use of organic solvents.

* * * * *